United States Patent [19]

Wallshein

[11] 4,028,809

[45] June 14, 1977

[54] BUCCAL END TUBE

[76] Inventor: Melvin Wallshein, 8645 Bay Parkway, Brooklyn, N.Y. 11214

[22] Filed: Mar. 30, 1976

[21] Appl. No.: 672,012

Related U.S. Application Data

[63] Continuation-in-part of Ser. No. 574,569, May 5, 1975, Pat. No. 3,988,831.

[52] U.S. Cl. .............................................. 32/14 A
[51] Int. Cl.$^2$ .......................................... A61C 7/00
[58] Field of Search .................................... 32/14 A

[56] References Cited

UNITED STATES PATENTS

| | | | |
|---|---|---|---|
| 3,119,182 | 1/1964 | Miller et al. ........................ | 32/14 A |
| 3,218,715 | 11/1965 | Wallshein .......................... | 32/14 A |

OTHER PUBLICATIONS

Ormco Catalogue, 816 Dodsworth Ave., Covita, Calif., Buccal Tubes, Mar. 27, 1968.

*Primary Examiner*—Robert Peshock
*Attorney, Agent, or Firm*—Flynn & Frishauf

[57] ABSTRACT

A buccal end tube with a pair of spaced apart arch wire positioning means, one positioning means defining at least one aperture and the other positioning means defining at least two apertures which are spaced apart in the buccal-lingual or occlusal-gingival direction, said apertures being adapted to receive spaced portions of an arch wire. The arch wire may be disposed in a predetermined orientation within a buccal-lingual or occlusal-gingival plane by positioning the arch wire in selected apertures of the spaced apart arch wire positioning means and is maintained in the selected orientation against the action of external forces applied both to the arch wire and to the buccal end tube device. The means defining the apertures preferably comprises a tab or divider means extending from and integral with a portion of the buccal end tube. A buccal end tube also comprises at least two hook members which are spaced apart in the longitudinal direction of the buccal end tube, the projecting portions of the hook members being directed toward each other. The hook members are preferably symmetrically located on the buccal end tube device.

18 Claims, 12 Drawing Figures

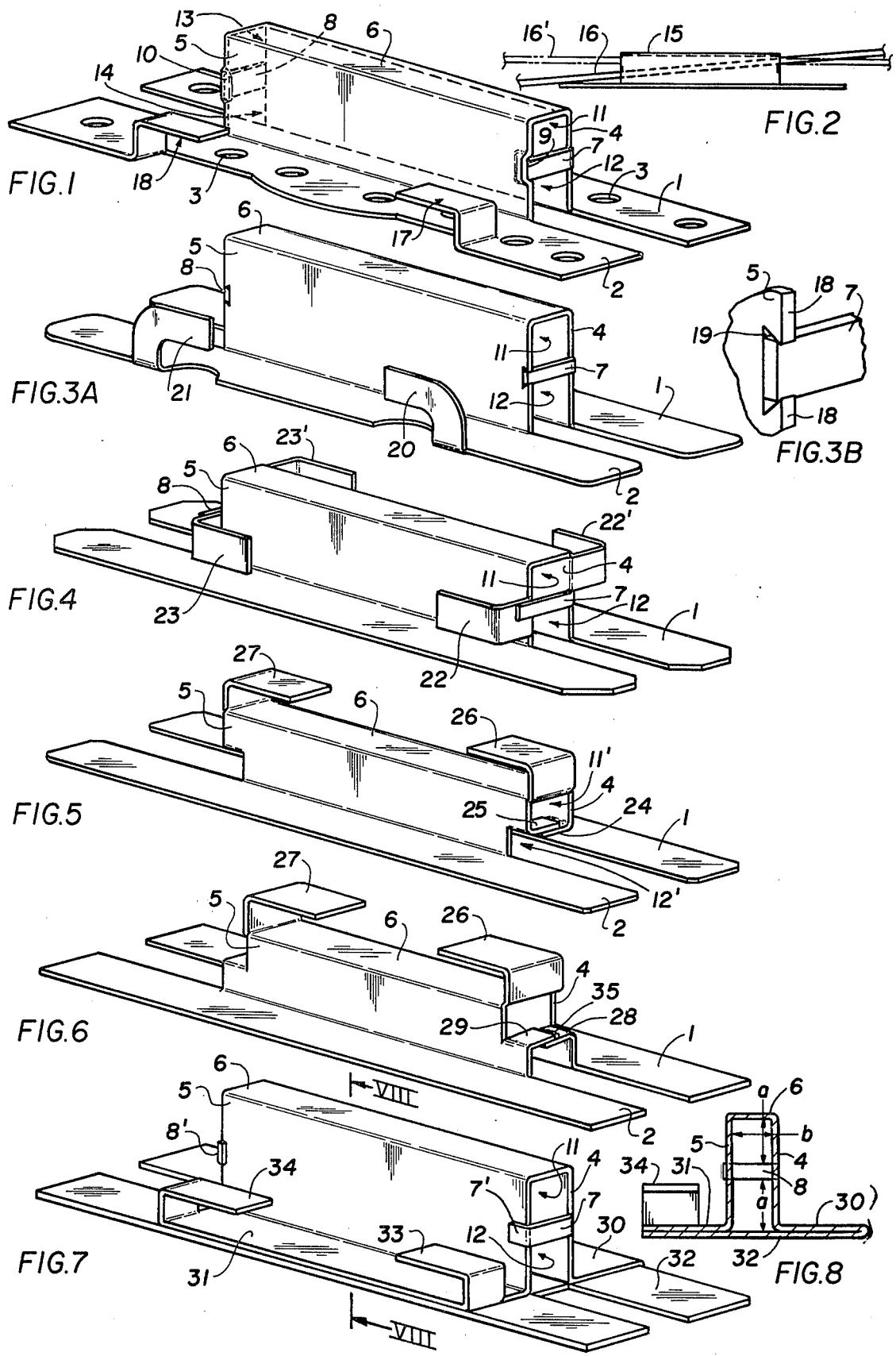

BUCCAL END TUBE

This is a continuation-in-part of application Ser. No. 574,569, filed May 5, 1975 and now U.S. Pat. No. 3,988,831 issued Nov. 2, 1976.

CROSS-REFERENCE TO RELATED PATENT

U.S. Pat. No. 3,874,080, issued Apr. 1, 1975 to Melvin Wallshein, the contents of which are incorporated herein by reference.

BACKGROUND OF THE INVENTION

The present invention relates to orthodontic appliances, and more particularly to an improved buccal end tube device for selectively orienting an orthodontic arch wire in a buccal-lingual or occlusal-gingival direction relative to a tooth on which the buccal end tube device is mounted, and to an improved buccal end tube having uniquely arranged hook members for engaging elastic orthodontic applicances.

A buccal end tube device for selectively orienting an orthodontic arch wire in different positions within a buccal-lingual plane is known from any above-mentioned U.S. Pat. No. 3,874,080.

In many instances it is required to use elastic orthodontic applicances in combination with arch wires and buccal end tubes. In such instances hook members are required to be mounted on the tooth for engagement with the elastic orthodontic appliance. However, no buccal end tube device incorporates such hook members in such a form that it is universally suitable for use in most applications, while still having the desired orthodontic characteristics. For example, devices are known having hooks extending outward toward the outer edge or from the outer edge of the device. Such hooks are engaged by extending an elastic orthodontic appliance along the length of the device and over the end of such hook. This causes application of rotational forces to the tooth, which in most instances is undesirable.

The main object of the present invention is to provide new constructions of such buccal end tube devices which may be more easily and advantageously fabricated.

A further object of the present invention is to provide a buccal end tube device having at least a pair of hook members which are better arranged for use with elastic orthodontic appliances. In connection with this object, a pair of hook members are spaced along the length of the buccal end tube and are directed toward each other so as to provide a universal structure which may be used in substantially any desired orientation on any tooth.

A further object of the present invention is to provide a buccal end tube which permits selective orientation of the arch wire in the buccal-lingual or occlusal-gingival plane, and which further incorporates such a universal-type hook member construction for cooperation with elastic orthodontic appliances.

A still further object of the present invention is to provide the above-types of buccal end tube devices which may be easily fabricated without requiring the stamping out of tiny apertures in a solid sheet of material, which is a difficult operation increasing the cost and complexity of my prior device.

SUMMARY OF THE INVENTION

In accordance with a first feature of the present invention, a buccal end tube device includes at least two spaced apart arch wire positioning means, one of the arch wire positioning means defining at least one aperture and the other of the arch wire positioning means defining at least two apertures which are spaced from each other in the buccal-lingual or occlusal-gingival direction, the apertures being adapted to receive spaced portions of the arch wire. The arch wire may be disposed in predetermined orientations within a buccal-lingual or occlusal-gingival plane by positioning the arch wire in selected apertures defined by the two spaced apart arch wire positioning means, and the arch wire is thereby maintained in the selected orientation against the action of external forces applied to both the arch wire and to the buccal end tube device.

According to a further aspect of the present invention, a buccal end tube is provided with spaced apart hook means which have hook members directed toward each other and toward the central portion of the buccal end tube. This construction enables engagement of the hook means by elastic orthodontic appliances while minimizing the application of undesirable rotational forces to the tooth. The hook means are spaced apart in the longitudinal direction of the buccal end tube.

In accordance with a still further feature of the invention, the mutually facing hook members are provided on only one side of the buccal end tube device and are symmetrically located so that the buccal end tube device may be utilized in any desired orientation relative to any tooth.

According to a still further feature of the invention, a buccal end tube device includes the above-mentioned novel arch wire positioning means in combination with the mutually facing, spaced apart hook members.

BRIEF DESCRIPTION OF THE DRAWINGS

FIG. 1 is a perspective view of a first embodiment of the present invention;

FIG. 2 is an illustration showing an arch wire engaged with a buccal end tube of the present invention in two different positions, illustrating the inventive concept;

FIG. 3A is a perspective view illustrating another embodiment of the invention;

FIG. 3B is an exploded view of a portion of the embodiment of FIG. 3A;

FIG. 4 is a perspective view of a still further embodiment of the present invention;

FIG. 5 is a perspective view of yet another embodiment of the present invention;

FIG. 6 is a perspective view of still another embodiment of the present invention;

FIG. 7 is a perspective view of a further embodiment of the present invention, illustrating a buccal end tube with a bottom member;

FIG. 8 is a sectional view of the embodiment of FIG. 7 taken along the line VIII—VIII;

DETAILED DESCRIPTION OF ILLUSTRATED EMBODIMENTS

Figure 9:
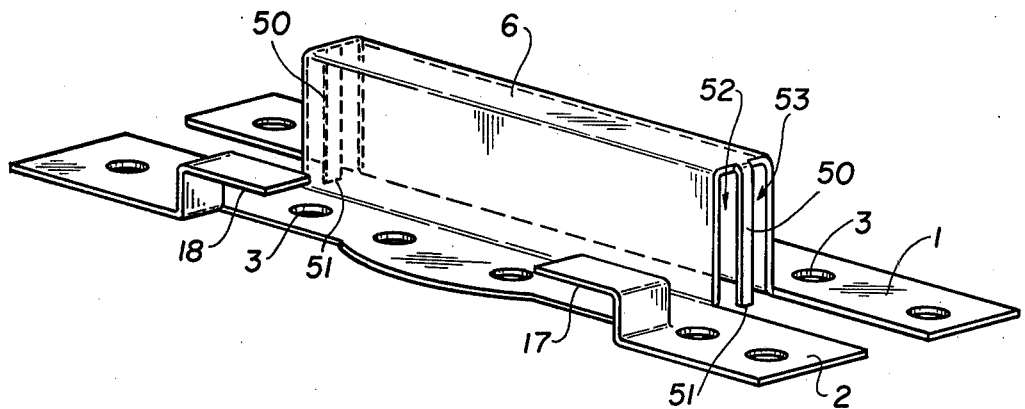
FIG. 9 is a perspective view of a still further embodiment of the present invention.

Referring to FIG. 1, a first embodiment of a buccal end tube device of the present invention comprises flanges 1,2 which are preferably in substantially the same plane and which are adapted to be either welded to an orthodontic band or directly cemented or otherwise secured to the buccal surface of a tooth. The holes 3 in flanges 1 and 2 are provided to cooperate with an adhesive when the appliance is secured directly to the buccal surface of a tooth. The number of holes 3 provided is not critical. The buccal end tube device further comprises upright members 4,5 which project respectively from the inner edges of flanges 1 and 2. The upright members 4 and 5 are shown substantially perpendicular to the flanges 1 and 2, but it should be clear that other orientations may be provided. A top portion 6 interconnects the upright members 4 and 5. Preferably, the flanges 1,2, the upright members 4,5 and top portion 6 are formed, for example, by bending a single piece of stamped-out material or by casting.

The buccal end tube further comprises a pair of dividers or tabs 7,8, hereinafter referred to as tabs for ease of description, which are preferably integral with the upright portion 4 and are bent over to the position shown in FIG. 1. The upright member 5 has a pair of internal depressions 9,10 formed therein, for example by an impacting operation, which are adapted to receive the free ends of the respective tabs 7,8. The depressions are suitably formed so that the non-depressed portions of the upright member 5 serve as a back-stop member to prevent excessive bending in of the tabe 7,8 and to prevent vertical movement of the free ends of tabs 7,8 relative to the upright member 5. While the tabs 7,8 are shown as extending from upright member 4, it should be clear that one or both of the tabs 7,8 can be fabricated to be integral with the upright portion 5, the associated depression 9,10 being made in the opposite upright member.

The upright members 4,5, top portion 6 and tabs 7,8 define first and second apertures 11,12 at the right hand end portion of the buccal end tube as seen in FIG. 1, and first and second apertures 13,14 at the oppsite end of the buccal end tube. Since the flanges 1,2 are adapted to be mounted on the buccal surface of a tooth, either directly or through the intermediary of an orthodontic band or the like, the apertures of each pair of apertures 11,12 and 13,14 are respectively spaced from each other in the buccal-lingual direction.

Referring to FIG. 2, a buccal end tube 15 fabricated in accordance with the present inventive concept is shown having an arch wire 16 passing therethrough so as to be inclined relative to the flanges of the buccal end tube (that is, relative to the buccal surface of the tooth). An arch wire 16', shown in chain lines in FIG. 2 is shown inserted through different apertures of the buccal end tube so as to be substantially parallel to the flanges thereof (that is, substantially parallel to the buccal surface of the tooth). The tabs 7,8, extending across an intermediate portion of the upright members 4,5 serve as an effective dividing means which defines the pairs of apertures at each end of the buccal end tube. By providing the depressions 9,10 in the upright member 5, the tabs are positively held in position and restrained from being moved responsive to forces applied thereon by the arch wire passing through the apertures.

In accordance with a further feature of the invention, the buccal end tube of the present invention comprises a pair of mutually facing hook members 17,18 which are spaced along the longitudinal direction of the buccal end tube device. In FIG. 1, the hook members 17,18 are integral with the flange 2 and are formed by a bending operation from the single sheet of stamped-out material. The free ends of the hook members 17,18 face each other. Preferably, the hook members are symmetrically located relative to the overall buccal end tube device and are located on only a single flange 2. In this manner, since the complete device is symmetrical, the buccal end tube may be rotated by 180° so as to locate the flange containing the hooks, if desired, as far as possible away from the occlusion.

Referring to FIGS. 3A and 3B, a further embodiment of the present invention is illustrated which is similar to the embodiment of FIG. 1 except for the configuration of the hook members and except for the means for retaining the tab members 7,8 positively in position. As shown in FIGS. 3A and 3B, the upright member 5 has an opening 19 therein for receiving the end portion of the tabs 7,8. The portions of the opening 19 at the end wall 18 of the upright member 5 are slightly smaller than the vertical dimension of the tab 7 (see FIG. 3B). The tab 7 is forcedly inserted into the opening 19 by snapping same passed the abutment defined by the end wall portion 18 of the upright member 5 so as to be positively locked in the opening 19. A similar construction is provided for tab 8 at the other end of the buccal end tube device. If desired, the end wall portion 18 need not define an opening smaller than the vertical height of the tab 7. In this event, the tab 7 will be merely bent so as to be received in the opening 19, without having an abutment means positively locking same in the opening 19.

The holes 3 shown in FIG. 1 may be provided in flanges 1 and 2 of the embodiment of FIG. 3A, as desired. With respect to the further embodiments of the invention illustrated in FIGS. 4–7 and discussed in detail hereinbelow, it should be clear that such holes 3 as illustrated in FIG. 1 may be provided in any or all of said embodiments, as desired.

In FIG. 3A, the buccal end tube device has a pair of spaced hook members 20,21 which mutually free each other (as in the embodiment of FIG. 1). In FIG. 3A, the hook members 20,21 are formed with only a single bend; that is, by merely bending same upwardly at the juncture between the flange 2 and the hook members 20,21.

FIG. 4 illustrates a further embodiment of the present invention wherein the tabs 7,8 are elongated and extend pasted the outermost vertical edge of the upright member 5. In this embodiment, the hook members 22,23 are formed integrally with the upright member 5 and are bent over as shown in FIG. 4 to provide the mutually facing spaced apart hook members of the present invention. As should be apparent, the hook members 22,23 and tabs 7,8 may be fabricated as extending from either of the upright members 4,5, the illustrated arrangement being shown merely by way of example. The tabs 7,8 may be merely bent so that they lie over the hook members 22,23 as shown in FIG. 4, or they may be welded or otherwise fixed at their free ends, for example by welding to the adjacent surface of the respective hook members and/or the upright member 5. The weld point is omitted for the sake of clarity.

One or both hook members 22', 23' may be provided for still more versatility.

FIG. 5 shows still a further embodiment of the invention whereby in the resulting configuration, the upright members 4,5 are generally T shaped. As shown in the right hand portion of the FIG. 5 embodiment, the tab member 7 is replaced by a pair of tab-portions 24,25 extending respectively from upright members 4 and 5. Tab-portions 24,25 overlap each other so as to effectively provide apertures 11',12', similar to apertures 11,12 of FIG. 1. The tab-portions 24,25 may be bent over so that they are adjacent each other or they may be welded or otherwise fixed to each other to provide a still more rigid structure. The opposite end of the buccal end tube is formed in a similar manner as the end having tab-portions 24,25, as should be apparent. Instead of overlapping each other, the free ends of tab portions 24,25 may merely abut each other or be adjacent each other in substantially the same plane.

In FIG. 5, the hook members 26,27 are integral with the top portion 6 and are bent over therefrom as illustrated so as to be mutually facing each other. In the embodiment of FIG. 5, the overall buccal end tube device is completely symmetrical, not only in the longitudinal direction, but also in the transverse direction. This means that the buccal end tube device of FIG. 5 will provide identical effects even when rotated 180° on the buccal surface of a tooth.

The embodiment of FIG. 6 is similar to that of FIG. 5 in that identical hook members 26,27 are provided. The upright members 4,5 are modified from those of FIG. 5 so that they provide an inverted "T" profile. Tab-portions 28,29 extend respectively from upright members 4,5 and overlap each other as illustrated. Alternatively, the free ends of tab portions 28,29 may abut each other to be adjacent each other in substantially the same plane. As mentioned above with respect to FIG. 5, tab-portions 28,29 may be welded together, for example as shown by weld 35, so as to provide a still more rigid overall structure. By adhering the overlapping portions of the tab-portions 28,29 together, better resistance against forces applied by the arch wire passing through the apertures is achieved. Also, by adhering the free end portions of the tab-portions 28,29 together, the upright members 4,5 are prevented from moving away from or toward each other.

In the above-described embodiments, the buccal end tube device was open at the bottom portion of aperture 12 so that the band to which the device was secured, or the buccal surface of the tooth itself, provided the "floor" or bottom of the device. If desired, the device may be provided with its own integral floor or bottom as shown in FIG. 7. FIG. 7 also illustrates a modified form of tabs 7,8, the tabs having end portions 7',8' which are bent around the outside of the upright member 5. The tabs 7,8 are preferably, integral with one of the upright members, for example member 4 as shown in FIG. 7. The device further comprises flanges 30,31 which are integrally formed with upright members 4,5 and which are bent over relative to the upright members 4,5. The flange 30 further has a floor or bottom member 32 integrally formed therewith and which is bent around so as to be substantially in a plane parallel to the phase of flange 30, as is more clearly seen from FIG. 8.

The flange 31 has extending portions which are bent over so as to form hook members 33,34 which are spaced along the longitudinal direction of the buccal end tube device and which are directed toward each other. The flanges 30,31, as well as the floor 32 may be provided with holes such as holes 3 of FIG. 1 for better engagement with cement, or the like, for use in cementing the device directly to a tooth. The holes 3 may be also advantageous when connecting the buccal end tube device to an orthodontic band or other intermediary for connection to a tooth.

The hook members 33,34 may alternatively be formed by bending extensions of the floor member 32 into a similar shape as any of the other illustrated hook members. The illustrated hook members are shown only by way of example, it being clear that the various hook members and tube arrangements may be used in any combination. While hook members are preferably integral with the tubes, they may be attached to the tubes or flanges.

By providing the depressions 9,10 which engage the tabs 7,8 as shown in FIG. 1, the upright members 4 and 5 are prevented from being bent toward each other, thereby preventing the buccal end tube device from buckling. Also, by virtue of the upper and lower edges of the depressions 9,10 preventing the free ends of the tabs 7,8 from moving up and down, the buccal end tube device is rendered more rigid so that it tends to resist tilting forces applied in a direction which tend to tilt the upright members 4,5. The embodiment of FIGS. 3A and 3B will also tend to resist such tilting forces. Likewise, the embodiment of FIG. 4 when the free ends of the tabs 7,8 are welded in place. The embodiment of FIG. 7, with the wrapped around ends 7',8', will provide resistance to a spreading apart movement of upright members 4,5. When the free ends of tabs 7,8 of FIG. 7 are welded or otherwise fixed in place, the resulting structure will also tend to resist tilting forces.

The above-described embodiments of the present invention are all, for example, made of a single piece of material stamped-out to the appropriate shape whereby simple bending operations may be used to form the resulting structures, or are made by casting, or other suitable techniques. When casting is used, the tabs or dividers may be cast integral with the tube at both ends of the respective tabs or dividers. There is no need in the embodiments shown in the drawings to form small and accurate apertures in solid members to define the arch wire positioning apertures. During the stamping operation, the material may be scored or otherwise deformed to define bending lines and to facilitate the bending operation. If desired, some of the bending operations can be performed simultaneously with the stamping operation.

In a preferred embodiment the dimensions $a$ and $b$ as shown in FIG. 8 are 0.028 inches and 0.022 inches, respectively. These dimensions are illustrative only and are given to stress the relatively small dimensions involved and the need for simplified, practical and economical manufacture.

Figure 10:
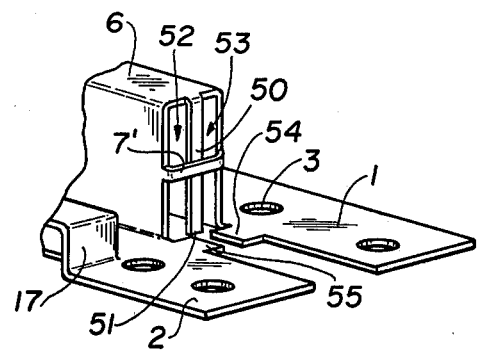
FIG. 10 is a perspective view of an embodiment of the present invention similar to that of FIG. 9.
Figure 11:
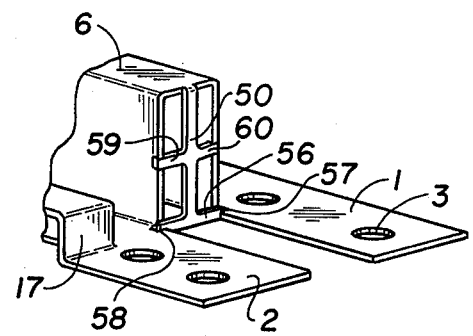
FIG. 11 is a partial perspective view of a still further embodiment similar to that of FIG. 9.

FIGS. 9, 10, and 11 illustrate various modifications of the invention which provide appertures for selective orientation of an arch wire in the occlusal-gingival plane. The embodiments of FIGS. 9 – 11 are, as described above with respect to FIG. 8, preferably fabricated of a single piece of material by cutting and bending same to provide the appropriate structural features. An integral downwardly extending tab portion 50 extends from an upper surface 6 of a buccal end tube, as shown in FIG. 9. In FIG. 9 the tab 50 is shown with a free end portion 51. In some instances, depending upon the material from which the end tube is made and depending upon the size and forces involved, this arrangement will provide adequate structural integrity. The flanges 1 and 2 are against the buccal surface of a tooth, either directly or via the intermediary of a band, so the arch wire which is inserted through openings 52 and/or 53 are retained therein.

As shown in FIG. 10, the flanges 1 and/or 2 may have inwardly directed portions 54, 55, through which the tab member 50 will snap in place when it is being bent to the position shown in FIG. 10. Alternatively, the tab member 50 may have a widened end portion 56 which could engage notches 57, 58 of the flanges 1 and 2, as shown in FIG. 11. In FIGS. 10 and 11, cross members 7' and 59,60 are provided to form spaced apertures also in the buccal-lingual direction. This enables arch wires to be inserted at a compound angle, that is, at a combination of various buccal-lingual, gingival-occlusal directions. One side of the buccal end tube may have apertures spaced in the buccal-lingual direction, and the other of the tube may have apertures spaced in the occlusal-gingival direction. Any combination of spaced apertures in various directions may be easily provided to produce a highly flexible buccal end tube.

The above arrangement provides a greatly improved buccal end tube for enabling arch wires to be inserted at various orientations in the occlusal-gingival plane. It is pointed out that the interior of the tube is free of dividing means so that the arch wire may pass freely in any selected orientation therethrough.

While the invention has been described above with respect to specific apparatus, numerous alterations of the structure herein disclosed will become apparent to those skilled in the art. The illustration of the preferred embodiment of the present invention is not to be construed as a limitation of the inventive concept as defined in the appended claims.

I claim:

1. A buccal end tube device for selectively orienting an orthodontic arch wire relative to a tooth, the buccal end tube device being adapted for mounting to a buccal surface of the tooth, the device comprising: at least two arch wire positioning means spaced apart from each other in the axial direction of said buccal end tube, one of said arch wire positioning means defining at least one aperture and the other of said arch wire positioning means defining at least two apertures which are spaced apart from each other in the occlusal-gingival direction, said apertures being adapted to receive spaced portions of the arch wire, said other of said arch wire positioning means comprising a dividing tab member connected to said buccal end tube forming means and extending across said buccal end tube in a direction substantially perpendicular to the occlusal-gingival direction of said tube, said dividing tab member cooperating with said buccal end tube for defining at least two apertures spaced apart from each other in said occlusal-gingival direction, whereby the arch wire may be disposed in a predetermined orientation within an occlusal gingival plane by positioning the arch wire in selected apertures of said at least two spaced apart arch wire positioning means and maintained in the selected orientation against the action of external forces applied both to the arch wire and to the buccal end tube device.

2. A buccal end tube device according to claim 1 wherein said dividing tab member extends across said buccal end tube device in a plane substantially perpendicular to said occlusal-gingival direction.

3. A buccal end tube device according to claim 1 wherein said dividing tab member is integral with said buccal end tube forming means and has at least one free end, and wherein said buccal end tube comprises respective means for engaging said free end.

4. A buccal end tube device according to claim 3 wherein said engaging means each comprise respective indentations in a portion of said buccal end tube device for receiving said free end of said dividing tab member.

5. A buccal end tube device according to claim 3 wherein said engaging means comprises cut-out portions in a wall of said buccal end tube device for receiving said free end of said dividing tab member.

6. A buccal end tube device according to claim 1 wherein each of said arch wire positioning means comprises at least one dividing tab member integral with and at opposite end portions of said buccal end tube.

7. A buccal end tube device according to claim 3 wherein each of said arch wire positioning means comprises at least one of said integral dividing tab members at opposite end portions of said buccal end tube.

8. A buccal end tube device according to claim 1, wherein at least one of said arch wire positioning means further comprises a cross member for defining at least two apertures spaced apart from each other in the buccal-lingual direction.

9. A buccal end tube device according to claim 8, wherein said other arch wire positioning means includes said cross member.

10. A buccal end tube device according to claim 9, wherein said one of said arch wire positioning means comprises a dividing tab member integral with said buccal end tube forming means extending across said buccal end tube in a direction substantially perpendicular to the occlusal-gingival direction of said tube for defining at least two apertures spaced apart from each other in said occlusal-gingival direction.

11. A buccal end tube device according to claim 9, wherein said one of said arch wire positioning means defines at least two apertures which are spaced apart from each other in the buccal-lingual direction.

12. A buccal end tube device according to claim 11, wherein said one arch wire positioning means comprises divider means extending across said buccal end tube device.

13. A buccal end tube device according to claim 1, wherein said dividing tab member comprises a bent-over integral extension of said buccal end tube.

14. A buccal end tube device for selectively orienting an orthodontic arch wire relative to a tooth, the buccal end tube device being adapted for mounting to a buccal surface of the tooth, the device comprising:
at least two arch wire positioning means spaced apart in the axial direction of the buccal end tube, one of said arch wire positioning means defining at least one aperture and the other of said arch wire positioning means defining at least two apertures which are spaced apart from each other in the buccal-lingual direction, said apertures being adapted to receive spaced portions of the arch wire;
at least one of said arch wire positioning means defining at least two apertures which are spaced apart from each other in the occlusal-gingival direction and which are adapted to receive spaced portions of the arch wire;

whereby the arch wire may be disposed in a predetermined orientation by positioning the arch wire in selected apertures of said at least two spaced apart arch wire positioning means and maintained in the selected orientation against the action of external forces applied both to the arch wire and to the buccal end tube device.

15. A buccal end tube device according to claim 14, wherein said arch wire positioning means each comprises divider means extending across said buccal end tube device.

16. A buccal end tube device according to claim 15, wherein said divider means are integral bent-over extensions of said buccal end tube device.

17. A buccal end tube device according to claim 16, wherein said buccal end tube device comprises engaging means for fixedly retaining said divider means in predetermined positions.

18. A buccal end tube device according to claim 1 wherein said dividing tab member of said other of said arch wire positioning means is integral with said buccal end tube forming means.

* * * * *